United States Patent [19]

Forward et al.

[11] Patent Number: 4,490,570
[45] Date of Patent: Dec. 25, 1984

[54] METHOD FOR PARA SELECTIVE ALKYLATION EMPLOYING SILICALITE CATALYSTS

[75] Inventors: Cleve H. Forward; James R. Butler; James M. Watson; Gary D. Branum, all of Big Spring, Tex.

[73] Assignee: Cosden Technology, Inc., Dallas, Tex.

[21] Appl. No.: 350,672

[22] Filed: Feb. 22, 1982

[51] Int. Cl.$^3$ ............................................. C07C 2/68
[52] U.S. Cl. .................................................. 585/467
[58] Field of Search ........................................ 585/467

[56] References Cited

U.S. PATENT DOCUMENTS 4,104,319  8/1978  Kaeding ............................ 585/467
4,238,318  12/1980  Kouwenhoven et al. ......... 208/120
4,283,306  8/1981  Herkes ............................... 585/467

FOREIGN PATENT DOCUMENTS 0021475  1/1981  European Pat. Off. .

OTHER PUBLICATIONS

Olson et al., *Journal of Catalysis*, 61, 390–396 (1980).

*Primary Examiner*—Curtis R. Davis
*Attorney, Agent, or Firm*—John K. Abokhair

[57] ABSTRACT

A process for the selective alkylation of a monoalkyl benzene in which the alkyl substituent is either methyl or ethyl, to yield a dialkylbenzene product in which the para isomer of the disubstituted product is present in a concentration greater than in a thermodynamic equilibrium is provided. The method essentially comprises passing the monoalkyl benzene and an alkylating agent capable of methylation or ethylation through a reaction zone containing a crystalline silica polymorph silicalite catalyst. Water, in the form of steam, can be co-fed as an option.

6 Claims, No Drawings

METHOD FOR PARA SELECTIVE ALKYLATION EMPLOYING SILICALITE CATALYSTS

TECHNICAL FIELD

This invention relates to a process for the production of dialkyl benzenes employing silicalite type catalysts. More specifically, a process is provided for the selective alkylation of monoalkyl benzenes, such as toluene and ethyl benzene, over a silicalite catalyst having catalytic activity, and in particular activity toward alkylating para to the existing alkyl group on the substituted benzene to yield a dialkyl benzene product in which the para isomer is present in an amount greater than would be present in a thermodynamic equilibrium isomer mix.

BACKGROUND ART

Various dialkyl benzenes, such as ethyltoluene and diethyl benzene, are used as important precursor compounds from which the corresponding vinyl aromatic monomers are made. The resulting monomers, i.e., vinyltoluene and divinylbenzene, are essential to the production of a variety of styrenic polymer materials. Additionally, xylene is a useful dialkyl benzene used in the production of terephthalic acid which is an important intermediate in the synthesis of synthetic fibers such as "Dacron".

In the case of diethyl benzene and ethyltoluene the para isomer is the most useful intermediate, with the ortho isomer being highly undesirable. Because of the undesirability of the ortho isomer, expensive distillation techniques must be employed prior to dehydrogenation of the ethyltoluene and diethylbenzene.

At present, many alkyl benzene conversion processes include processing steps wherein the aromatic substrates which are to be converted are contacted under conversion conditions in the presence of catalyst materials. Both single and multiple bed catalyst processes are well known in the art. An important property to be considered in the selection of the catalyst is the selectivity of the catalyst to the desired product. A subcategory of the selectivity of the catalyst to the desired product is the selectivity of the catalyst to the desired isomer of the desired product, for example, para selectivity. Various aluminosilicate type zeolite catalysts, including those known as "ZSM" catalysts, have been reported to be suitable for selectively producing para substituted benzene derivatives upon being modified for that purpose. One problem with these types of catalysts, however, is that they are subject to rapid deactivation in the presence of even small amounts of water. Rapid deactivaation means that a high rate of conversion of reactants to products cannot be maintained over a long period of time thus requiring expensive catalyst changeouts or regeneration procedures which greatly reduce the efficiency of the overall process. Thus, in using such catalysts it is sometimes necessary to reduce the moisture content of the feed stock materials prior to their introduction to a conversion zone.

Another problem with the aluminosilicate type catalyst is that they must often be modified with "promoters" to obtain significantly increased para selectivity. In other words, these types of catalysts have little or no intrinsic para selectivity, i.e. the catalysts must be modified before they will produce a product in which the para isomer is present in an amount greater than in a thermodynamic equilibrium. The thermodynamic equilibrium concentration for isomers of ethyl-toluene is about 31.5% para, about 50.2% meta and about 18.3% ortho at normal operating conditions for vapor phase alkylation.

As noted earlier, the para isomer of the dialkylbenzenes is the most useful intermediate, with the ortho isomer being the most undesirable. A need exists, therefore, for a method for selectively producing para dialkylbenzenes in amounts greater than that present in a thermodynamic equilibrium mix.

Recently, catalysts characterized as crystalline silica polymorphs prepared in accordance with specified procedures and known generically as "silicalite" type catalysts, have been discovered to be useful in aromatic conversion processes. These catalysts are not subject to deactivation in the presence of steam and, in some cases, as set forth in our now abandoned co-pending application Ser. No. 06/255,882, steam actually enhances the stability of these materials during alkylation.

SUMMARY OF THE INVENTION

In accordance with the present invention, a process for the selective alkylation of monoalkyl benzenes to yield a dialkyl benzene product in which the para isomer is present in an amount greater than in a thermodynamic equilibrium is provided. Utilization of the process disclosed herein results in excellent product and isomer selectivity, as well as high conversion rates and low rates of deactivation. Further, the silicalite type catalysts employed in the present invention exhibit intrinsic paraselective properties, and, therefore, may be used without special treatment or other modification prior to use. Further, it has been discovered that by controlling the temperature during conversion process which employ silicalite catalysts within a range of from about 350° C. to 500° C., better para selectivity and stability can be attained.

The method of the present invention comprises contacting the reactants to be converted in the presence of a crystalline silica polymorph catalyst of the silicalite type under conversion conditions. In the preferred embodiment of the present invention, aromatic substrates such as toluene and ethylbenzene are alkylated with an alkylating agent, such as ethylene, by contacting the aromatic substrate and alkylating agent in the presence of a crystalline silica polymorph silicalite catalyst under alkylation conditions. The silicalite catalyst material need not be modified in any manner and water in the form of steam may be co-fed as an option, if desired. By operating within the temperature range specified above, the para selectivity of the unmodified silicalite catalyst can be maintained without rapid deactivation of the catalyst.

DETAILED DESCRIPTION

In accordance with the present invention, a method is provided for the selective alkylation of monoalkyl benzenes to produce a dialkyl benzene product in which the para isomer is present in an amount greater than in a thermodynamic equilibrium. The process essentially comprises feeding the monoalkyl benzene and an alkylating agent to a reaction zone containing a crystalline silica polymorph catalyst of the silicalite type under controlled conversion conditions. The monoalkyl benzene is either toluene or ethylbenzene and the alkylating agent can be any alkylating agent capable of effecting methylation or ethylation under conversion conditions. The desired dialkyl products produced are either xylene, diethylbenzene or ethyltoluene. In one preferred embodiment, the monoalkyl benzene is toluene, the alkylating agent is ethylene and the dialkyl product, therefore, is ethyltoluene.

The process of the present invention can be carried out using a variety of process equipment, including a reactor vessel having a hydrocarbon conversion zone which contains the silicalite catalyst material. Either single or multiple catalyst beds can be employed in the reaction zone. The reactants can be admixed and preheated prior to introduction into the reaction zone where they contact the catalyst beds under conversion conditions further specified hereinbelow. If desired, steam can be admixed with the reactants just prior to their introduction into the reaction zone. After a controlled residence time within the reaction zone, the converted hydrocarbon charge passes out of the reactor where the desired products are collected by cooling or other standard recovery techniques.

The mole ratio of hydrocarbon reactants will be controlled in accordance with the desired reaction products. Pressures and weight hourly space velocities of the reactants passing through the conversion zone will be the major factors affecting residence time (and, therefore, contact time with the silicalite catalyst material) within the zone. The temperatures specified herein are measured as an average inlet temperature of the conversion zone during steady state operation.

The catalyst material employed by the process of the subject invention is a true crystalline silica material as opposed to a zeolitic material, which, by definition, is a silicate of aluminum and either sodium or calcium, or both, which demonstrates ion exchange capacity. The crystalline silica materials used as catalysts in the present invention are silica polymorphs whose structures have been designated as "silicalite". These materials, in contrast to aluminosilicate zeolites, demonstrate no appreciable ion exchange properties since $AlO_4^-$ tetrahedra do not comprise a portion of the crystalline silica framework. Aluminum may be present in these silicalite catalyst materials as a result of impurities in the silica source used to prepare the catalyst, but silicalite containing such aluminum or other oxide impurities can in no sense be considered a metallosilicate. Further description and methods for preparing silicalite type catalysts are set forth in U.S. Pat. No. 4,061,724, the entire disclosure of which is incorporated herein by reference.

In addition to the physical distinctions between the crystalline silica polymorph silicalite type catalyst and more conventional aluminosilicate zeolites, several functional distinctions are also apparent as regards to the use of these materials as hydrocarbon conversion catalysts. For example, ZSM-type aluminosilicate zeolites are reported to rapidly lose their catalytic activity in the presence of even minor amounts of water. As noted hereinabove, the crystalline silica polymorph silicalite materials of the present invention are useful hydrocarbon conversion catalysts even in the presence of steam and, in some instances, performances of the process can be enhanced through the use of a steam co-feed. Further, the crystalline silica polymorph silicalite type catalysts utilized in the process of the present invention exhibit intrinsic para selective properties and need not be modified in order to produce a dialkyl product in which the para isomer is present in an amount greater than in a thermodynamic equilibrium. Thus the catalysts useful in the present invention are unmodified in the sense that no special chemical, thermal or steam pretreatment of the catalyst as synthesized is necessary prior to its use in the described process.

In the preferred embodiment, toluene feedstock is alkylated by contacting same with ethylene in the presence of silicalite catalyst materials under conversion conditions. Conversion inlet temperatures should range between about 300° C. and 600° C., with temperatures of between about 370° C. and 450° C. being preferred. Surprisingly, it has been discovered that the para selectivity of the silicalite catalyst increases as the temperature decreases. This is truly unexpected in light of prior art relating to aluminosilicate zeolites which teaches that para selectivity increases as temperature increases. By employing these conditions, increased activity, as measured by the precentage of monoalkyl benezene feedstock converted to desired dialkyl substitute benzene product is obtained and improved stability can be achieved. Steam co-feed can also be employed, if desired.

Generally, the reaction of monoalkyl benzene feedstocks with alkylating agents is run with a substantial molar excess of monoalkyl benzene in order to reduce the incidence of polyalkylation. Preferred reactant molar ratios are from about 2:1 to about 20:1, monoalkyl benzene: alkylating agent. Pressure of from about atmospheric to about 25 atmospheres can be employed with preferred monoalkyl benzene WHSV's of from about 50 to about 200. Higher WHSV's, providing greater kinetic control of the process, may also be useful.

The process of the subject invention, which employs silicalite type catalysts, provides an especially efficient procedure for producing para-ethyltoluene, para-diethylbenzene and para-xylene. When employing the subject process to produce ethyltoluene from toluene aromatic feedstock, the preferred silicalite catalysts are those having a crystallite size of less than about eight microns and a silica to alumina ratio of at least about 200. The crystallite size of the silicalite catalyst is most preferably less than about 2 microns. Preferred reactant ratios are between about 7:1 and 18:1, with the preferred monoalkyl benzene WHSV's ranging from about 100 to about 150. Further operating conditions include preferred pressures a range of from about 10 to 15 atmospheres being preferred. Inlet temperature within the preferred range of from about 350° C. to about 450° C. are also employed.

If steam co-feed is desired, the preferred amount is from about 20,000 to about 60,000 parts per million, based on the amount of aromatic compound, with 40,000 parts per million steam co-feed being especially preferred.

The process of the present invention can be further exemplified through a study of the following examples which are not intended to limit the subject invention in any manner.

EXAMPLE I

Toluene and ethylene are introduced into a reaction zone containing a bed of silicalite catalyst material having a particle size of between 12 and 20 mesh and a bed depth of approximately 8.25 centimeters. The toluene to ethylene molar feed ratio is approximately 18:1. Three separate runs are performed in which the inlet reaction temperature is varied from approximately 475° C. to 460° C. and finally to approximately 450° C. In each instance, pressures of approximately 11 atmospheres, WHSV's of 130 and steam in the amount of 40,000 PPM, toluene based on the weight of the toluene, are employed. The product stream from the alkylation reaction zone is analyzed by gas chromatography. The catalyst activity is determined both at the start and at the end of the run according to the following formula:

$$\% \text{ Conversion} = \frac{\text{moles desired alkyl aromatic compound}}{\text{moles of reactive alkene fed to reactor}} \times 100\%$$

The selectivity is determined according to the following formula:

$$\text{Selectivity} = \frac{\text{weight desired alkyl aromatic compound}}{\text{total product weight}} \times 100\%$$

The silicalite catalyst utilized in this example has an $Al_2O_3$ binder, a crystallite size of about 2 microns, and a silica to alumino ratio of about 250.

EXAMPLE II

In this example, ethyltoluene is produced from a feedstock of toluene and ethylene fed to a reaction zone containing a bed of silicalite catalyst material having a particle size of between 12 and 20 mesh and a bed depth of approximately 7.62 centimeters. The molar ratio of toluene to ethylene is approximately 15:1. Six separate runs are performed in which the inlet reaction temperatures vary from approximately 490° C. to 445° C. In each instance, pressures of approximately 11 atmospheres, toluene WHSV's of 130, and steam in an amount of about 40,000 PPM based on the weight of toluene are employed. The silicalite catalyst used in each of these runs has a crystallite size of about 1-2 microns, an $Al_2O_3$ binder and a silica to alumina ratio of approximately 320.

EXAMPLE III

In this example, ethyltoluene is produced from a feedstock of toluene and ethylene fed to the reaction zone in a molar ratio of approximately 7:1. The catalyst bed depth is approximately 7.62 centimeters and the particle size is between 12 and 20 mesh. The catalyst has a crystallite size of about 1-2 microns, an $SiO_2$ binder and a silica to alumina ratio of about 320. One run is performed in which the inlet reaction temperature is approximately 445° C. The pressure is approximately 11 atmospheres, WHSV is 130 but no steam is utilized.

The results of all the examples are set forth below in Table I.

TABLE I

| Ex. | Run | Temp. (°C.) | Steam (ppm) | % Conversion | % Selectivity | para/meta/ortho | Cat. Age (hrs.) |
|---|---|---|---|---|---|---|---|
| I | 1 | 474 | 40,000 | 94.5 | 97.9–89.7 | 75.5/22/2.5 | 0–24 |
| I | 2 | 462 | 40,000 | 97.1 | 89.7–82.3 | 82/16/2 | 24–49 |
| I | 3 | 455 | 40,000 | 97.9 | 79.4–78.0 | 85.4/13/1.6 | 49–71 |
| II | 1 | 492 | 40,000 | 94.5 | 88.8 | 60/39.7/0.3 | 0–24 |
| II | 2 | 479 | 40,000 | 98.5 | 93.4 | 64.8/34.9/0.3 | 24–48 |
| II | 3 | 465 | 40,000 | 101 | 95.3 | 68.2/31.7/0.1 | 48–72 |
| II | 4 | 454 | 40,000 | 100 | 96.4 | 71.3/28.5/0.2 | 72–96 |
| II | 5 | 443 | 40,000 | 101 | 97.63 | 76.1/23.8/0.1 | 96–121 |
| II | 6 | 492 | 40,000 | 98.7 | 94 | 66.9/33/0.3 | 121–141 |
| III | 1 | 446 | None | 89–52 | 92.3–97.6 | 88.45/11.53/.02 | 0–12 |

The data in Table I indicates that the silicalite catalyst has substantial intrinsic para selective properties which increase as a function of time and as temperature decreases. The percent of para toluene present in the resulting product is significantly greater than the thermodynamic equilibrium of a mixture of ethyltoluene isomers, which is 31.4%. Further, the para selectivity of these catalysts at very short catalyst age indicates the selectivity is not due to carbon deposition but rather is intrinsic to these materials.

As stated above, the para selectivity of the silicalite catalyst increases as the temperature decreases. It should be noted that although part of this increase in para selectivity can be attributed to the increase in the age of the catalyst, the increase in para selectivity when the temperature is reduced far exceeds the contribution to para selectivity attributed solely to catalyst age. For example, during Run 6 of Example II, the temperature is returned to the initial run temperature of 492° C. from the 121st to the 141st hour. The increase in the para selectivity of this particular catalyst attributable solely to catalyst age is approximately 7% (from 60% to 66.9%) over the 141 hours. When the temperature is steadily reduced in the other five runs, the increase in para selectivity is about 16% (from 60% to 76.1%) over only 121 hours. Thus, even though increased catalyst age enhances para selectivity, the range of the temperature of the reaction, being run 6 of Example II, actually caused a decrease in para production as compared with runs 3-5 using catalysts of less age and lower temperatures.

One of ordinary skill in the art upon reading the above specification and examples will appreciate that the process of the subject invention can be modified or adapted in a variety of ways. All such modifications or adaptations which fall within the scope of the appended claims are intended to be covered thereby.

What is claimed is:

1. A process for the selective alkylation of a monoalkyl benzene in which the alkyl substituent is either methyl or ethyl, to yield a dialkyl benzene product in which the para isomer of the disubstituted product is present in a concentration greater than in a thermodynamic equilibrium, comprising:

passing the monoalkyl benzene and an alkylating agent capable of methylation or ethylation under conversion conditions which do not include steam cofeed through a reaction zone containing an unmodified crystalline silica polymorph silicalite catalyst.

2. The process as recited in claim 1 wherein the alkylating agent is ethylene.

3. The process as recited in claim 1 wherein the monoalkyl benzene is toluene.

4. The method as recited in claim 1 wherein the conversion conditions comprise temperatures in the range of from about 300° C. to about 600° C., a molar feed ratio of monoalkyl benzene to alkylating agent between about 2:1 to about 20:1, a monoalkyl benzene WHSV ranging from about 50 to about 200 and pressures ranging from about atmospheric to about 25 atmospheres.

5. The process as recited in claim 4 wherein the temperature range is from about 350° C. to about 450° C., the molar feed ratio range is from about 7:1 to about 18:1, the pressure range is from about 11 atmospheres to about 13 atmospheres and the monoalkyl benzene WHSV range is from about 120 to about 200.

6. A process for producing dialkyl benzene products comprising:

(a) introducing to a reaction zone containing a bed of a crystalline silica polymorph silicalite catalyst a monoalkyl benzene and an alkylating agent;
(b) allowing said monoalkyl benzene and alkylating agent to come into contact with said silicalite catalyst material under conversion conditions which do not include steam cofeed; and
(c) recovering from said reaction zone a dialkyl benzene isomer mix comprising a greater than thermodynamic equilibrium amount of the para-isomer thereof.

* * * * *